US00PP10121P

United States Patent [19]

VandenBerg

[11] Patent Number: Plant 10,121

[45] Date of Patent: Nov. 18, 1997

[54] CARNATION PLANT NAMED JAZZ

[75] Inventor: Cornelis P. VandenBerg, Salinas, Calif.

[73] Assignee: Yoder Brothers, Inc., Barberton, Ohio

[21] Appl. No.: 608,624

[22] Filed: Mar. 1, 1996

[51] Int. Cl.[6] ..... A01H 5/00

[52] U.S. Cl. ..... Plt./70.2

[58] Field of Search ..... Plt./70.2

[56] References Cited

U.S. PATENT DOCUMENTS

P.P. 5,445 4/1985 Barberet et al. ..... Plt./70

*Primary Examiner*—James R. Feyrer
*Assistant Examiner*—Melissa L. Kimball
*Attorney, Agent, or Firm*—Foley & Lardner

[57] ABSTRACT

A carnation plant named Jazz particularly characterized by its commercial double flower type; flat flower form; orange flower color with non-uniform and inconsistent red markings on petals and petal margins; diameter of flower of 55 to 57 mm when fully opened, when grown as a spray carnation; petal margins are slightly serrated and ruffled; strong, flexible stems; high production of flowers, with 5 to 7 flowering laterals developing per stem; flowering response to 25 to 26 weeks after planting rooted cuttings; very resistant to *Fusarium oxysporum*; and recommended as miniature (spray) carnation.

1 Drawing Sheet

The present invention comprises a new and distinct cultivar of carnation, botanically known as *Dianthus caryophyllus* L. and referred to by the cultivar name Jazz.

Jazz, identified as 2565 (89-332001), was originated from a cross made under the supervision of Cornelis P. VandenBerg in a controlled breeding program in Salinas, Calif., in September of 1985.

The female parent of Jazz was the variety identified as Starlight, and described as a red spray carnation.

The male parent of Jazz was the variety identified as Shiro, and described as a white standard (disbudded) carnation.

The breeding program resulting in Jazz has as objective to create new carnation cultivars resistant to *Fusarium oxysporum*. In order to ensure resistance, seedlings were planted in a controlled environment in soil heavily infested with *Fusarium oxysporum* in Suba, near Bogota, Colombia, South America. Seedlings were allowed to grow to flowering stage, with removal of those seedlings that died from *Fusarium oxysporum*.

Jazz was discovered and selected as one flowering plant within the progeny of the stated cross by Cornelis P. VandenBerg in October of 1989, in the above described location.

The first act of asexual reproduction of Jazz was accomplished when vegetative cuttings were taken from the initial selection in Suba, Colombia in October of 1989, immediately after selection, by technicians working under supervision of Cornelis P. VandenBerg.

Horticultural examination of controlled flowerings of successive plantings has shown that the unique combination of characteristics as herein disclosed for Jazz are firmly fixed and are retained through successive generations of asexual reproduction.

Jazz has not been observed under all possible environmental conditions. The phenotpe may vary significantly with variations in environment such as temperature, light intensity and daylength, without, however, any variance in genotype.

The following observations, measurements and comparisons describe plants grown in Suba, near Bogota, Colombia, under greenhouse conditions which approximate those generally used in commercial greenhouse practice.

The following traits have been repeatedly observed and are determined to be basic characteristics of Jazz, which, in combination, distinguish this carnation as a new and distinct cultivar:

1. Commercial double flower type.
2. Flat flower form.
3. Orange flower color with non-uniform and inconsistent red markings on petals and petal margins.
4. Diameter of flower of 55 to 57 mm when fully opened, when grown as a spray carnation.
5. Petal margins are slightly serrated and ruffled.
6. Strong, flexible stems.
7. High production of flowers, with 5 to 7 flowering laterals developing per stem.
8. Flowering response of 25 to 26 weeks after planting rooted cuttings.
9. Very resistant to *Fusarium oxysporum*.
10. Recommended as miniature (spray) carnation.

The accompanying photographic drawing shows a typical inflorescence of Jazz, grown as a spray cut carnation, with the colors being as nearly true as possible with illustrations of this type.

Of the commercial cultivars known to the inventor, the most similar in comparison to Jazz is the cultivar Victoria, disclosed in U.S. Plant Pat. No. 8,971. Similar traits are flower type and form, flower color, resistance to *Fusarium oxysporum*, and the recommendation to grow as a spray carnation. Jazz has more intense markings on petals and petal margins than Victoria. Jazz is slightly slower in flower response than Victoria. The foliage of Jazz is wider and longer than the foliage of Victoria.

In the following description color references are made to The Royal Horticultural Society Colour Chart. The color values were determined on plant material grown as spray carnations at Suba, Colombia, and shipped to Salinas, Calif., on Jan. 25, 1996.

Classification:

*Botanical.*—*Dianthus caryophyllius* L. cv Jazz.

*Commercial.*—Spray carnation for cut flower production.

INFLORESCENCE

*Form.*—Flat.

*Type.*—*Commercial double.*

*Flower diameter.*—55 to 57 mm when fully opened.

*Number of petals.*—27 to 32.

*Color (general tonality from a distance of three meters)* .—Orange, with red markings.

*Color (upper surface)*.—33D, with markings 45C; base white with 145C.

*Color (under surface)*.—26D, markings 45C.

*Shape*.—Rounded, slightly serrated and ruffled.

*Calyx*.—Color between 144A and 144B.

*Androecium*.—Normal to semi-petaloid stamens; normal to degenerated anthers; moderate pollen.

*Gynoecium*.—Typical carnation, smooth, conical ovaries; 2 to 3 styles.

*Fragrance*.—Slight fragrance, typical carnation.

*Fertility*.—Functions as both seed parent and pollen parent.

*Keeping quality*—14 to 17 days after cutting and transportation.

PLANT

A. General appearance:

*Growth*.—Bushy, semi erect perennial; plant is normally pinched approximately three weeks after planting to produce upright habit typical of cut carnations.

*Branching*.—Semi-erect, numerous and unrestricted at base of plant; 5 to 7 flowering laterals developing per stem.

*Height*.—Two (2) year old plants may reach 150 to 200 cm in height.

B. Foliage:

*Color*.—Typical carnation, between 133A and 189A, overlaid with 189B.

*Texture*.—Surface has a thin wax-like bloom which is bluish green in color.

*Size*.—Mature leaves are 10 to 16 cm in length and 7 to 10 mm in width; weakly curled.

*Shape*.—Long, narrow, lancet shaped.

Flowering: The first flush of flowers appears 25 to 26 weeks after planting rooted cuttings, and there are approximately 4 to 5 flowering stems at first flush when the apical bud is removed. The side laterals then grow out in approximately 8 to 9 weeks, after which the second flush of flowers appears. The flowers of the first and second flushes are similar in size, but in subsequent flushes the flowers tend to become somewhat smaller. There are approximately 5 to 6 flushes of flowers during a two year plant life, at which time a commercial plant would typically be discarded.

What is claimed is:

1. A new and distinct carnation plant named Jazz, as described and illustrated.

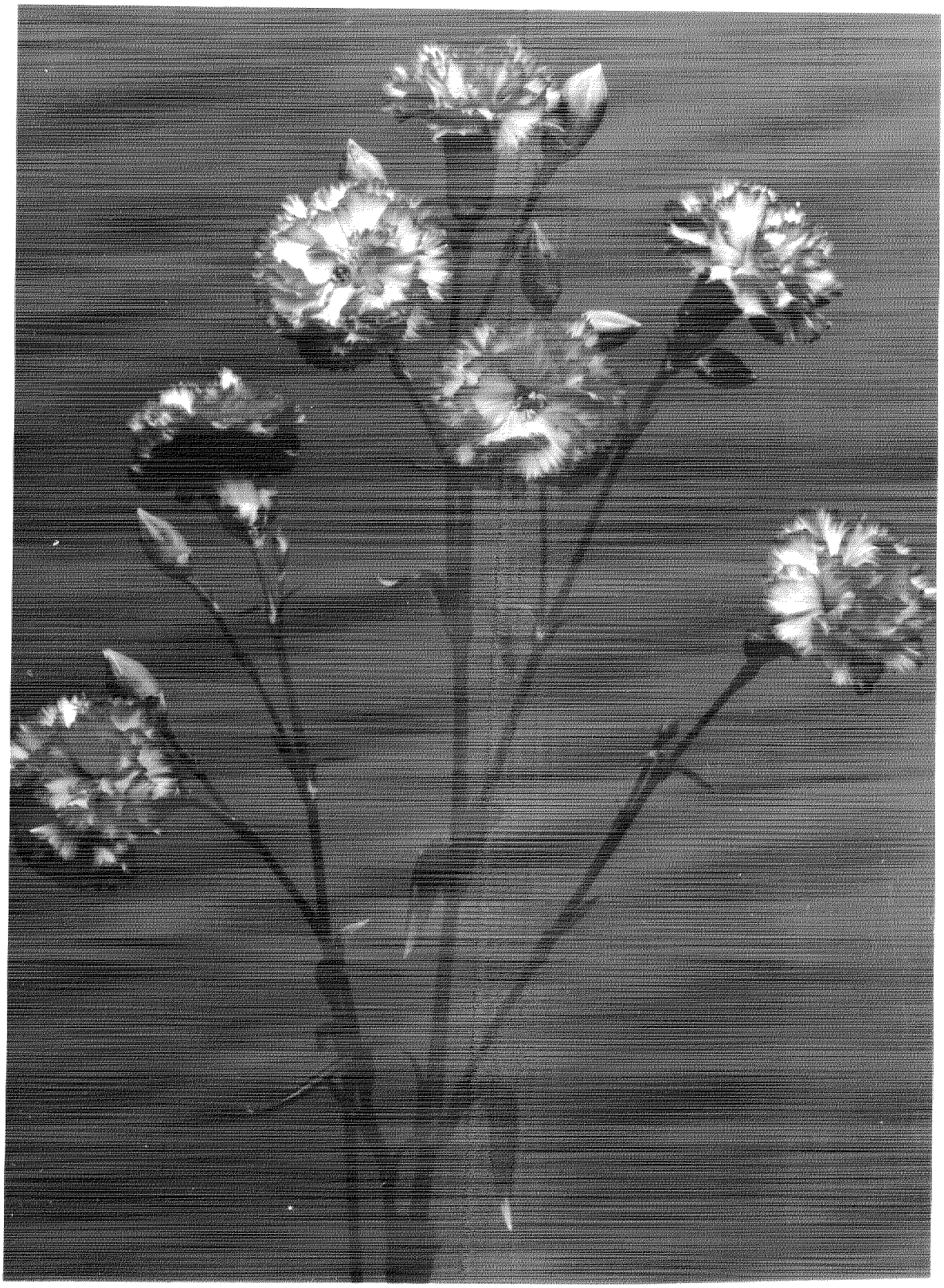

* * * * *